April. 1, 1969 F. W. ANDERSON Plant Pat. 2,879
NECTARINE TREE
Filed Oct. 16, 1967
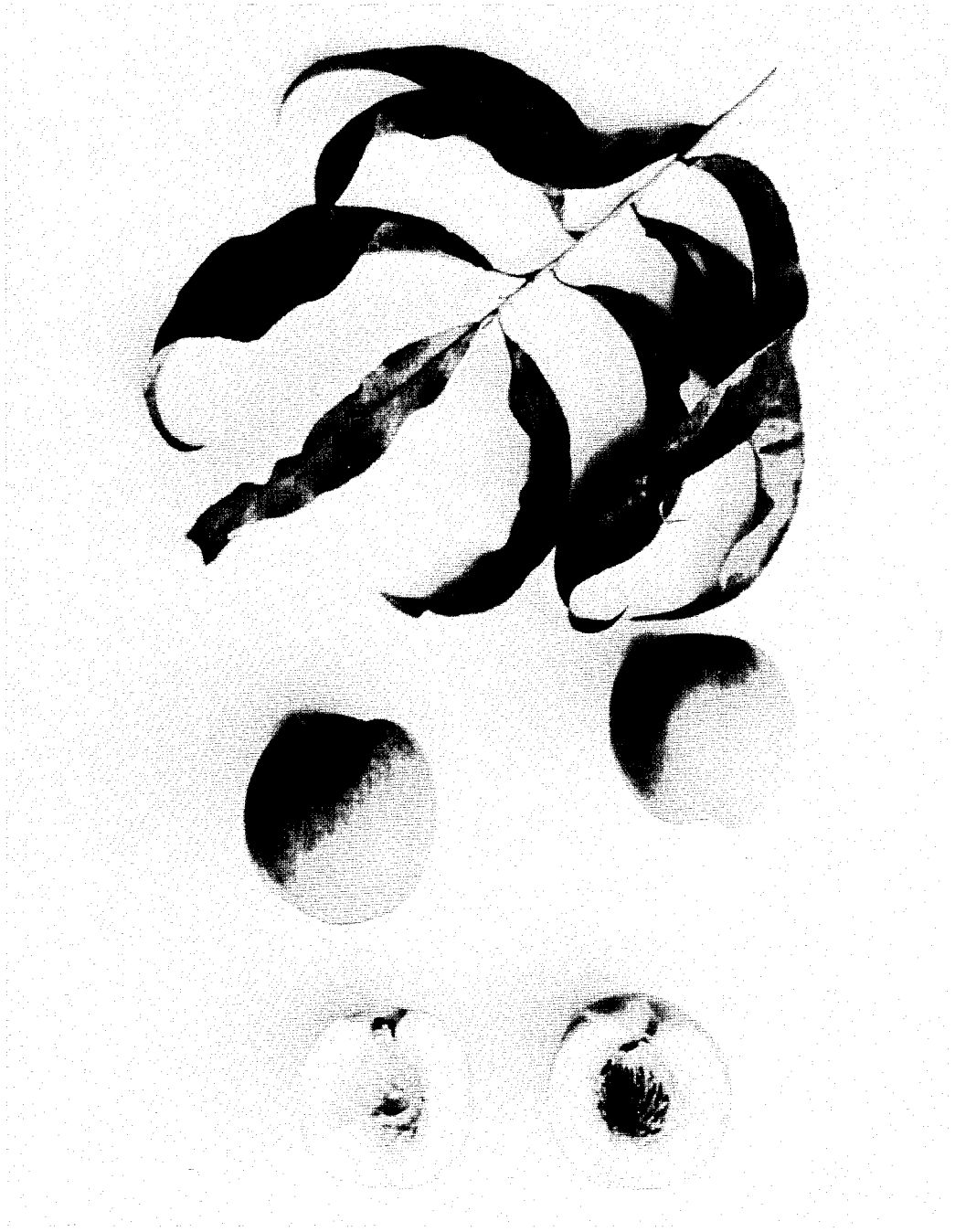
INVENTOR
Frederic W. Anderson
BY Webster & Webster
ATTORNEYS United States Patent Office Plant Pat. 2,879
Patented Apr. 1, 1969

2,879
NECTARINE TREE

Frederic W. Anderson, Merced, Calif., assignor to Reedley Nursery, Inc., Reedley, Calif., a corporation of California Filed Oct. 16, 1967, Ser. No. 675,719
Int. Cl. A01h 5/08
U.S. Cl. Plt.—41 1 Claim

ABSTRACT OF THE DISCLOSURE

A variety of nectarine tree which is a regular and very productive bearer of large, uniform, globose fruit—of freestone type—having yellow flesh, and yellow skin substantially overspread with red. The variety is embraced by Group III (with bitter kernels) of the classification established by Caillavet and Souty in their Monographie des Principales Variétés de Pêchers, 1950 edition.

*Background of the variety*

Over a substantial number of years I have engaged in an extensive and continuing plant breeding program at my experimental nursery and orchard located near Le Grand, Merced County, Calif.; the purpose of such program being to provide improved varieties of fruit trees. The present variety of nectarine tree resulted from my endeavors in the conduct of such plant breeding program.

*Origin of the variety*

The present variety of nectarine tree was originated by me, at my experimental nursery and orchard located as aforesaid, as a cross between Late Le Grand nectarine (United States Plant Patent No. 1,035) and Early Sun Grand nectarine (United States Plant Patent No. 1,420). One seedling of such cross, and which is the instant variety, evidenced desirable characteristics and was, therefore, selected by me for asexual reproduction, preparatory to commercialization.

*Asexual reproduction of the variety*

Subsequent to origination of the variety, as above, I asexually reproduced it by top-working on mature trees in my aforementioned orchard. In maturity, all of such reproductions ran true to the original tree in all respects.

*Summary of the variety*

The herein claimed variety of nectarine tree, which has general resemblance to the Sun Grand (United States Plant Patent No. 974) tree and its fruit, is distinctively characterized—in comparison—by an average larger size of fruit, by fruit having a more attractive overall physical appearance, and by reniform instead of globose glands on the leaves.

The instant variety of nectarine tree is further distinctively characterized by the bearing of large, globose, freestone fruit having yellow flesh, and yellow skin substantially overspread with red, and which fruit ripens about three weeks before the Le Grand (United States Plant Patent No. 549) and about with the Sun Grand.

*Brief description of the drawing*

The drawing is an illustration, by photographic reproduction in color, of a twig with leaves, and detached fruit; one fruit being cut in half to expose the flesh, and with the stone remaining in one cut half.

*Description of the variety*

The botanical details of this new and distinct variety of nectarine tree—with color definitions reference to Maerz and Paul Dictionary of Color—are as follows:

Tree:

*Size.*—Large.
*Vigor.*—Vigorous.
*Growth.*—Spreading.
*Production.*—Very productive.
*Bearing.*—Regular bearer.

Trunk: Size—medium.

Branches:

*Size.*—Medium.
*Texture.*—Medium.

Leaves:

*Size.*—Large to medium. Length—4½"–5". Width—1⅛"–1¼".
*Form.*—Lanceolate; acutely pointed.
*Margin.*—Crenate.
*Petiole.*—Medium length.
*Glands.*—Position and number—usually 2 on petiole and 1–3 on blade. Medium size; reniform.
*Color.*—Top side—Medium green (22–L–7). Under side—Lighter Green (21–L–7).

Flower buds: Size—medium.

Flowers:

*Blooming period.*—Date of first bloom—Mar. 10, 1967. Date of full bloom—Mar. 15, 1967. Medium, as compared with other varieties.
*Size.*—Large.

Fruit:

*Maturity when described.*—Eating ripe.
*Date of first picking.*—July 15, 1967.
*Date of last picking.*—July 24, 1967.
*Size.*—Large. Average diameter axially–2½". Average transversely in suture plane–2½".
*Form.*—Uniform; symmetrical; globose.
*Suture.*—Distinct.
*Ventral surface.*—Rounded slightly.
*Cavity.*—Medium depth; medium breadth.
*Base.*—Rounded.
*Apex.*—Short; depressed.

Skin:

*Thickness.*—thick to medium.
*Texture.*—Tough to medium.
*Tendency to crack.*—None.
*Down.*—Wanting.
*Color.*—Yellow (10–L–6) substantially overspread with Red (5–L–6 to 6–L–6), mottled and streaked darker Red (7–L–4).

Flesh:

*Amygdalin.*—Wanting.
*Juice.*—Moderate.
*Texture.*—Firm; meaty.
*Fibers.*—Few.
*Ripens.*—Evenly.
*Flavor.*—Subacid.

*Aroma.*—Distinct to wanting.
*Eating quality.*—Good to best.
*Color.*—Yellow (10–L–5). Surface of pit cavity—Red (5–K–5).

Stone:

*Type.*—Free.
*Size.*—Large to medium. Average length—1¼″. Average breadth—1″. Average thickness—¾″.
*Form.*—Globose to oval.
*Sides.*—Equal.
*Ridges.*—Rounded.
*Kernel.*—Bitter.
*Color.*—Brown (8–L–7).

Use: Market; dessert.

Keeping quality: good.
Shipping quality: Good.

The nectarine tree and its fruit herein described may vary in slight detail due to climatic and soil conditions under which the variety may be grown; the present description being of the variety as grown in the Central Valley of California, and wherein in 1967 all fruit ripened two weeks later than normal.

I claim:

1. A new and distinct variety of nectarine tree, substantially as illustrated and described , which is a regular and very productive bearer of large, globose, freestone fruit having yellow flesh, and yellow skin substantially overspread with red; the tree and its fruit generally resembling the Sun Grand but is distinctively characterized in comparison by an average larger size of fruit, by fruit having a more attractive overall physical appearance, and by reniform instead of globose glands on the leaves; and further distinctively characterized by fruit which ripens about three weeks before the Le Grand and about with the Sun Grand.

No references cited.

ROBERT E. BAGWILL, *Primary Examiner.*